United States Patent [19]

Chiou

[11] Patent Number: 5,492,130
[45] Date of Patent: Feb. 20, 1996

[54] BIOPSY DEVICE AND METHOD

[76] Inventor: Rei-Kwen Chiou, 11516 Hornfair Ct., Potomac, Md. 20854

[21] Appl. No.: 53,827

[22] Filed: Apr. 29, 1993

Related U.S. Application Data

[63] Continuation of Ser. No. 709,824, Jun. 4, 1991, abandoned.

[51] Int. Cl.$^6$ .................................................. A61B 10/00
[52] U.S. Cl. .......................... 128/753; 128/754; 606/170
[58] Field of Search .................................... 128/753, 754,
128/751, 752, 755; 606/167, 170, 184;
604/118, 119, 121, 187, 236, 238, 256

[56] References Cited

U.S. PATENT DOCUMENTS

| 4,256,119 | 3/1981 | Gauthier | 128/754 |
|---|---|---|---|
| 4,338,934 | 7/1982 | Spademan | 604/167 |
| 4,356,828 | 11/1982 | Jamshidi | 128/754 |
| 4,549,554 | 10/1985 | Markham | 128/753 |
| 4,643,196 | 2/1987 | Tanaka et al. | 128/753 |
| 4,699,154 | 10/1987 | Lindgren | 128/754 |
| 4,702,261 | 10/1987 | Cornell et al. | 128/754 |
| 4,747,414 | 5/1988 | Brossel | 128/754 |
| 4,776,346 | 10/1988 | Beraha et al. | 128/754 |
| 4,817,631 | 4/1989 | Schnepp-Pesch et al. | 128/753 |
| 4,838,282 | 6/1989 | Strasser et al. | 128/754 |
| 4,893,635 | 1/1990 | de Groot et al. | 128/754 |
| 4,917,100 | 4/1990 | Nottke | 128/749 |
| 4,944,308 | 7/1990 | Akerfeldt | 128/751 |
| 4,967,762 | 11/1990 | DeVries | 128/753 |
| 5,014,717 | 5/1991 | Lohrmann | 128/754 |
| 5,025,797 | 6/1991 | Baran | 128/754 |
| 5,172,701 | 12/1992 | Leigh | 128/753 |
| 5,183,052 | 2/1993 | Terwilliger | 128/753 |

FOREIGN PATENT DOCUMENTS

| 10321 | 4/1980 | European Pat. Off. | 128/754 |
|---|---|---|---|
| 0173653 | 3/1986 | European Pat. Off. | |
| 1551362 | 3/1990 | U.S.S.R. | 128/754 |

Primary Examiner—Stephen C. Pellegrino
Assistant Examiner—Guy V. Tucker
Attorney, Agent, or Firm—Thomas P. Liniak

[57] ABSTRACT

An improved biopsy needle is disclosed in a negative pressure biopsy needle comprising a cannula axially mounted to an elongated chamber with an inner solid stylet initially positioned with a cutting tip externally of the cutting edge of the cannula and extending axially through the elongated chamber exteriorly to an enlarged plunger with an annular plug mounted on an intermediate section of the stylet within the elongated chamber, whereby on relative movement of the elongated chamber and cannula away from the plunger, negative pressure will be effective within the cannula as it penetrates into tissue to core a biopsy. A spring biased mounting device is also provided to initially hold the cannula, elongated chamber and inner stylet and to move the elongated chamber and cannula relative to the inner stylet on firing a holding means. A novel method of coring a biopsy while simultaneously applying a negative pressure within the cannula to draw in and hold the biopsy in the cannula while the cannula is withdrawn from a tissue body is also disclosed.

18 Claims, 2 Drawing Sheets

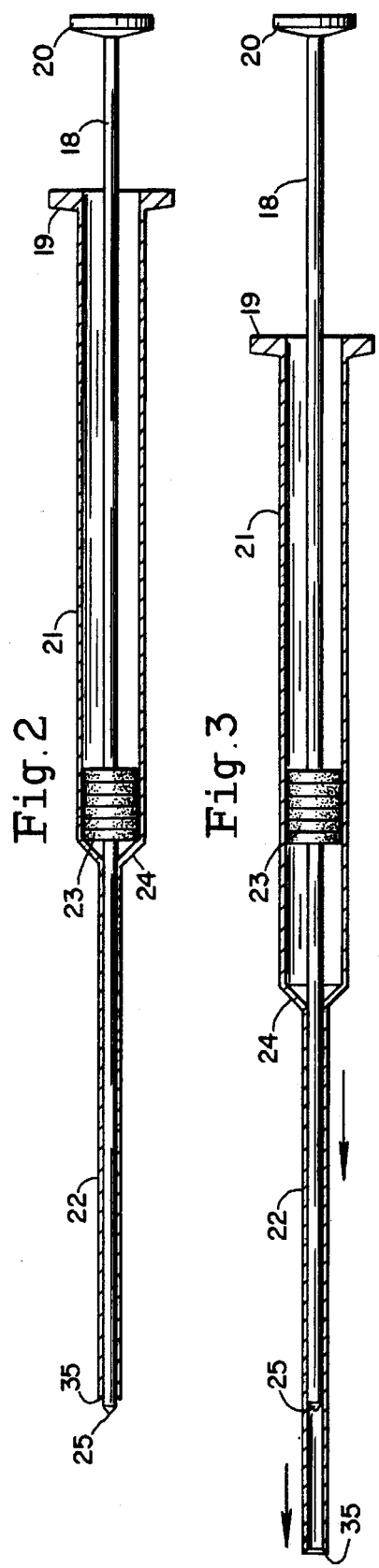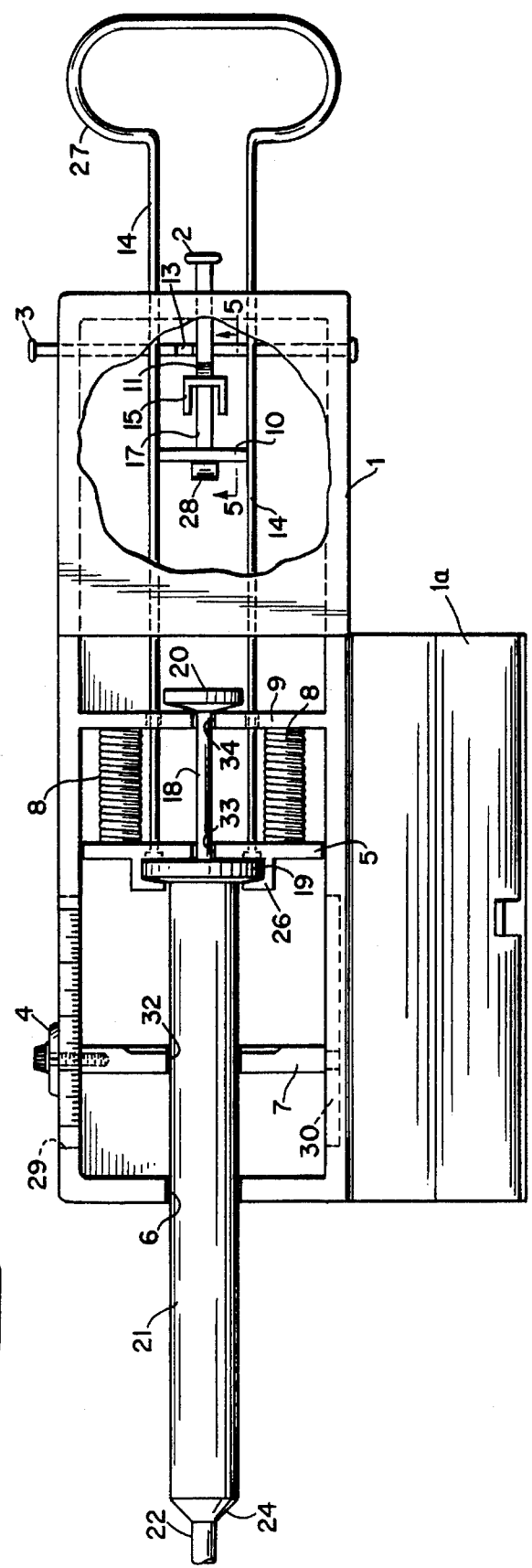

BIOPSY DEVICE AND METHOD

This is a continuation of application Ser. No. 07/709,824, filed on Jun. 4, 1991, now abandoned.

FIELD OF INVENTION

The present invention relates to an improved biopsy device and method of coring a biopsy. More particularly, the invention relates to a device and method having a new biopsy needle mechanism that enables one to obtain an equal or larger sized tissue sample for pathological examination in better condition than existing biopsy devices, while using a smaller caliber or diameter needle than those existing biopsy devices.

BACKGROUND OF THE INVENTION

Biopsy involves the sampling of the inner tissue of humans and animals for subsequent analyses and examination. Biopsy processes which are minimally intrusive are being increasingly used by doctors. Instead of using open surgery to cut off a piece of tissue for examination, physicians have been using needle mechanisms of various devices to obtain pieces of tissue without open surgery. Various manual devices have been used in the past. Many of these devices invariably had compartments that open and close in the tissue to be sampled, to entrap a piece of specimen. For example, the devices that have been used for the biopsy of prostate include the Veenema-Gusberg prostate biopsy cup, Franklin-Silverman biopsy needle (both manufactured by American V. Mueller), and the Travenol TRU-CUT biopsy needle. The Veenema-Gusberg prostate biopsy cup consists of a 0.5 cm diameter cup at the tip of the device. In operation, by opening and closing the cup after inserting it in the prostate, a piece of tissue is obtained by severing it and enclosing it. The Franklin-Silverman biopsy needle is used for the biopsy of kidney, liver, prostate, lymph gland, and thyroid tissues. It contains an inner split needle, the blade of which separates after entering the organ. The sheath is then advanced to close off the blades and to trap the specimen in the device. The most commonly used manual device is the Travenol TRU-CUT biopsy needle. The Travenol TRU-CUT biopsy needle consists of a notched stylet and a needle sheath. The Travenol mechanism operates by first advancing a stylet into the tissue, and then advancing a needle sheath over the stylet. A piece of tissue will then be trapped in the notch of the stylet as the stylet is retracted into the sheath, and can be retrieved for examination.

The aspiration method has also been used to obtain tissue samples for examination. The aspiration biopsy method operates by advancing a needle into the tissue to be sampled using a needle guide, and then using a syringe device to connect with the needle and aspirate samples into the needle. The advantage of the aspiration method is that fine (small diameter) needles can be used. The drawback is that only liquid samples, rather than a piece of tissue can be obtained, and one can only examine the cells in the liquid (cytology), while in pathology, both the cells and the structure are examined. Since the aspiration method is much less intrusive than other known sampling methods, it is less painful to the patient, and has fewer side effects. That is because the smaller the biopsy needle or instrument, the less likely it is to cause complication and pain.

In recent years, mechanical devices have been designed and combined with biopsy devices to provide quicker action and a cleaner cut of a tissue specimen. The basic principle behind these devices is that a cleaner, more precise cut can be made by utilizing a mechanical or electro-mechanically driven device, rather than the one controlled by the human hand. These spring-loaded biopsy devices such as those found in U.S. Pat. Nos. 4,776,346; 4,702,261; 4,699,154 and 4,917,100 generally utilize needles with a biopsy mechanism similar to that of the Travenol TRU-CUT biopsy needle.

Although the use of a spring-loaded biopsy device has advantages over the use of manual devices, the use of these biopsy mechanisms still poses certain limitations of the previously referred to notch type biopsy devices. For example, it is necessary for the size of the biopsy needle to be of a relatively large caliber to allow for a notch therein that is capable of obtaining a specimen large enough to enable proper testing. The size of the notch in turn is limited by the size of the overall device in an effort to make the biopsy procedure as noninvasive as possible. Since the solid portion of the stylet occupies a significant portion of the lumen, the size of the tissue obtained is considerably smaller than the diameter of the needle. Since the needle is fired under a mechanical force, the needle must also have sufficient strength and therefore size especially in the narrowed notch area, so that there is no significant risk of breaking the needle during the process. This specimen is sometimes too small for adequate examination and therefore requires the invasive biopsy procedure to be repeated until a sufficient sample is obtained.

In the present invention when a tissue sample is taken, the stylet does not remain in the section of the biopsy lumen that retains the tissue sample obtained from the biopsy at the end of the procedure. Thus, the full lumen of the biopsy needle can be filled with the specimen. The present invention therefore can provide an equal or larger size of specimen by using a significantly smaller sized needle than prior known devices. A smaller sized needle is less invasive and therefore likely to cause less pain and fewer complications.

Furthermore, in a biopsy needle that contains a notched stylet, the notched portion is usually the thinnest and weakest portion. This type of structure can be potentially dangerous when the needle encounters resistance to its travel. When it is fired with a spring-loaded device, the stylet part can bend or even break, which can cause very serious complications. These factors further limit how small a biopsy needle can be made. For these reasons, most physicians do not use current devices for deep organ biopsies and for lesions adjacent to large blood vessels. The present invention, which uses no notched stylet and has the capacity to obtain larger sized tissue samples with a smaller sized, structurally stronger needle, also provides a greater variety of uses as a result.

SUMMARY OF THE INVENTION

Accordingly, it is an object of the present invention to provide a novel biopsy device and method of use that is less invasive, yet provides a larger and better tissue sample then existing devices.

To further assist in drawing a negative pressure about the core of a biopsy within a cannula by a piston plug and vacuum chamber, it is a further object of the present invention to provide a spring actuated mounting device to hold the novel biopsy needle and to trigger the spring to drive the cannula and distal vacuum chamber relative to the inner stylet and piston plug, whereby accurate control of time of actuation and depth of penetration of cannula into the tissue and simultaneous drawing of negative pressure about the cored biopsy is attained.

It is yet another object of the present invention to provide an apparatus and method of applying a negative pressure of sufficient force along the annular spacing between the stylet and the outer hollow needle to draw the biopsy sample into the outer hollow needle and to hold it there during cutting and withdrawal of the biopsy sample from the tissue.

These and other objects are accomplished by operation of a novel biopsy device and method of use having a leading hollow cannula axially mounted to a vacuum chamber, with an internal solid stylet slidable therethrough, and having a piston plug mounted to the stylet to slide within the vacuum chamber, whereby movement of the cannula and vacuum chamber relative to the inner stylet and piston plug will simultaneously core a biopsy and produce a negative pressure between the cannula, as disclosed in relation to the following figures.

BRIEF DESCRIPTION OF THE DRAWINGS

FIG. 1 illustrates a typical prior art device for cutting a biopsy sample using an outer cannula with an inner stylet having a notched section.

FIG. 2 is a longitudinal cross-sectional view of the preinsertion arrangement of one embodiment biopsy needle of the present invention FIG. 3 is a longitudinal cross-sectional view similar to FIG. 2, illustrating one embodiment of the present invention in the tissue coring position.

FIG. 4 is a top view in partial section of a biopsy needle of the present invention mounted within a spring activated device for firing the biopsy needle to a predetermined depth.

DETAILED DESCRIPTION OF THE INVENTION

Figure 6:
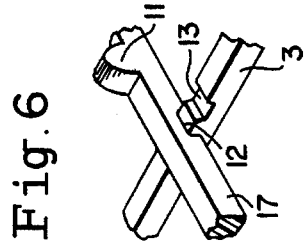
FIG. 6 is a partial perspective view of the spring-activated device of the present device, illustrating a security bar in locked position relative to the firing bar.

Referring now to the drawings and particularly FIGS. 2 and 3, the basic arrangement of the preferred embodiment of the biopsy device 50, according to the present invention, is illustrated.

Device 50, as illustrated in FIG. 2, features an outer hollow needle or cannula 22 having a sharpened cutting edge 35 at one end for insertion into tissue for sampling, and channel 36 that accommodates a tissue sample and provides housing for stylet 18. Cutting edge 35 of cannula 22 may be smooth or jagged and may be cut on an angle or at a right angle to the central axis of cannula 22. In preferred embodiments cutting edge 35 is jagged for reasons described later. Cutting edge 35 may be sharpened, such that it is on either the external surface or internal surface of cannula 22, or on a circumference between the inner and outer surfaces. Channel 36 of device 50 is connected by intermediate annular section 24 to one end of integral enlarged air chamber 21. Intermediate section 24 may be an annular truncated cone or a flat disc having a central aperture as long as the aperture is wide, but of a smaller diameter than chamber 21. Chamber 21 has flared annular flange 19 at its end opposite intermediate section.

Solid stylet 18 extends from outside of annular flange 19 through the entire length of chamber 21 and into channel 36, and is movable within chamber 21 and channel 36, in a manner that allows stylet 18 to selectively protrude from channel 36. Stylet 18 has sharpened point 25 on one end and integral enlarged plunger head 20 at the other end. Stylet 18 and cannula 22 are generally constructed of solid stainless steel or aluminum. Although many different sizes can be used, the diameter of stylet 18 varies preferably from 0.70 to 1.67 mm (0.027 to 0.066 inches), and its length varies from 12 cm to 37 cm. Cannula preferably has a diameter on the order of 0.032 to 0.083 inches (from 21 to 14 gauge). Smaller versions of device 50 may be used when performing biopsies on children. Point 25 of stylet 18 may be sharpened to various cutting angles. If the cannula 22 is sharpened with cutting edge 35 on the internal surface, as previously described, then the slope of the cutting surface may be continued onto point 25 of stylet 18 to form a continuous conical cutting surface which will permit a smoother initial insertion into tissue.

Plug 23, having outer sealing layer 38, is secured to stylet 18 and positioned between inner surface 39 of chamber 21 and stylet 18, such that plug 23 is tightly engaged yet slidable by movement of stylet 18 relative to inner surface 39 of chamber 21, in a manner to produce a negative pressure within variable gap 37 of chamber 21 and the annular space of channel 36 between stylet 18 and cannula 22. Plug 23 is preferably constructed of either a metal, ceramic, elastomer, rubber, or a plastic material. Regardless of its material construction, plug 23 is provided with an outer surface that will permit a slidable, substantially air tight surface between the inner wall of chamber 21 and plug 23, such that relative movement of chamber 21 to plug 23 will produce a negative pressure within variable gap 37. Plug 23 is mounted to stylet 18 by various mounting means, such as press fitting onto stylet 18, welding of plug 23 if the plug is formed from a metal, or by bonding with an adhesive. Plug 23 may also be formed of an annular inner core of any of the above materials, with an outer annular sealing layer of a resilient or elastomeric material bonded to the annular inner core.

Operation of device 50 in its simplest mode can be accomplished by hand. Device 50 (see FIGS. 2 and 3) is first inserted into the tissue of human or animal to be sampled to a desired depth, usually up to 17 cm, with point 25 of stylet 18 protruding from cannula 22, and with point 25 primarily used as a puncturing and cutting element, such that a sample of at least 1 cm in length is obtained. Cannula 22 and chamber 21 are then moved forward (further into the body), relative to stylet 18 which is kept stationary, resulting in the coring of a tissue sample, using edge 35 as a cutting element.

As shown in FIG. 3, movement of chamber 21 and cannula 22 into tissue to be sampled while stylet 18, and therefore plug 23, are held stationary, producing an increased negative pressure in enlarged zone 37 between plug 23 and cannula 22 and in cannula 22. This increased negative pressure is sufficient to draw, detach and held a biopsy sample within lumen 36 of cannula 22, as device 50 cuts a tissue sample and subsequently is withdrawn from the tissue with said biopsy sample contained therein. As previously mentioned the preferred cutting edge 35 of cannula 22 is jagged such that edge 35 can detach the end of the cored biopsy sample by very slight movement of device 50.

The use of a negative pressure biopsy needle in its simplest form as shown in FIGS. 2 and 3 merely requires holding stylet 18 in position, by means of stylet head 20, while advancing cannula 22 into tissue to be sampled by moving upper chamber 21 toward the sample. Since chamber 37 under plug 23 is expanded by movement toward the body of upper chamber 21 relative to plug 23 on stylet 18, a zone of reduced or negative pressure is produced therein, which reduced pressure zone functions to reduce pressure in said annular zone between stylet 18 and cannula 22, and also about cored biopsy in lumen 26 formed by downward movement of cannula 22. Reduced pressure about the biopsy tissue sample functions to further draw in and hold biopsy tissue sample within cannula 22, since the external zone about cannula 22 is at a higher ambient pressure.

Although device 50 can be operated by hand, it is preferred to use device 50 in conjunction with a firing device to provide very exact control over the depth and rate of penetration and withdrawal of biopsy device 50.

In order to provide a controlled means to both produce a negative pressure and a controlled penetration of the cannula 22 into the tissue, negative pressure biopsy needle is mounted within firing device 1 shown, more particularly in FIGS. 4 through 7. Mechanical firing device 1, designed to support and operate negative pressure biopsy device 50 shown in FIGS. 2 and 3, comprises access door 1a hinged or otherwise mounted to an outer shell 40. Access door 1a of firing device 1 of shell 40 may be hinged or formed with inwardly disposed flexible opposed sides that will function to snap into the sides of the opening into shell 40 of firing device 1. Upper chamber 21, cannula 22 and mounting head 19 are removably positioned in the following slots of firing device 1: lower slot 6 in the bottom of shell 40 of said firing device 1 for receiving chamber 21, stop plate slot 32 in stop plate 7 for receiving chamber 21, semi-annular slot 26 for engaging with mounting head 19, intermediate slot 33 in firing plate 5, and upper slot 34 in fixed base plate 9 for receiving stylet 18 and holding stylet plunger 20 thereabove, and to provide firing or downward movement of chamber 21 and cannula 22 relative to stylet 18, spring device 8 is mounted between fixed base plate 9 and movable firing plate 5. Spring device 8 may be comprised of either a single large spring or of several smaller springs mounted about the biopsy needle.

Figure 5:
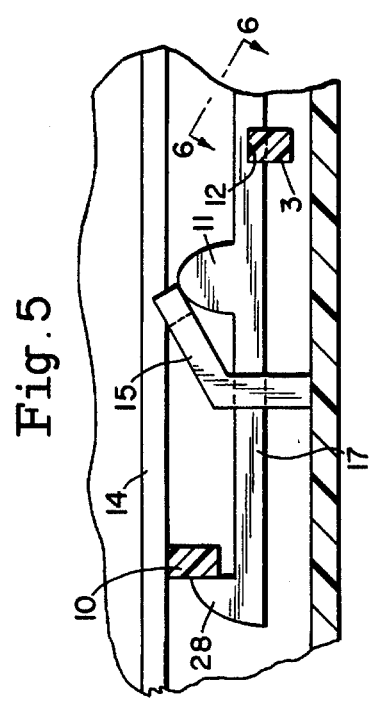
FIG. 5 is a partial sectional view of a trigger release mechanism for holding the spring-activated device of the present invention in a prefiring position with a security bar in a locked position.
Figure 7:
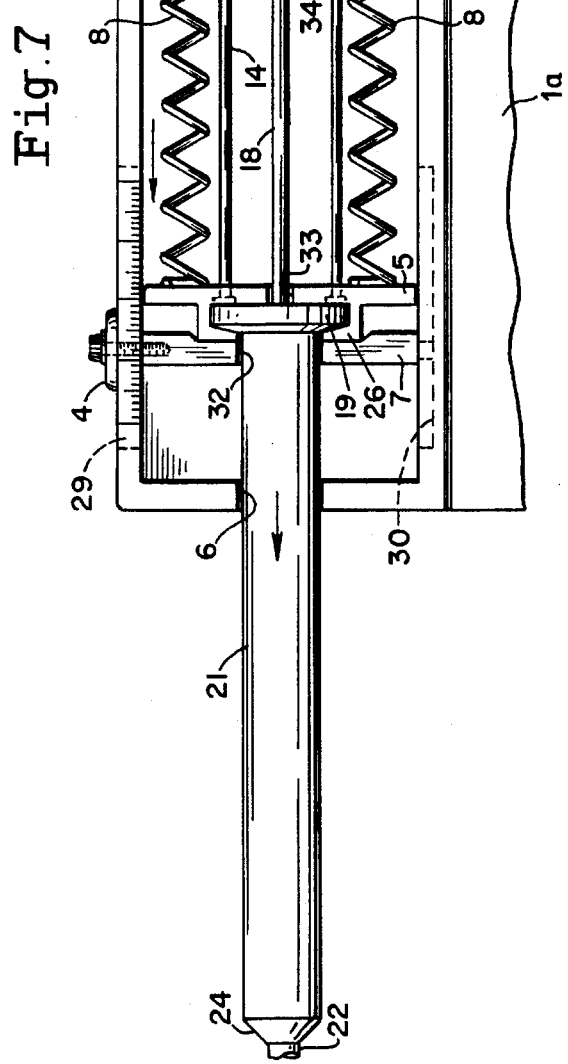
FIG. 7 is a top view in partial section similar to FIG. 4, showing the spring activated device of the present invention in extended position after firing of the biopsy needle.

To permit loading of spring device 8, spaced parallel rods 14 are secured to firing plate 5, and extend upwardly through openings 41 in base plate 9 and apertures 55 in the top of shell of mechanical device 1 where rods 14 are joined together with an intermediate loading cross bar 10 and an upper curved portion to form pull ring 27. To secure spring-biased firing plate 5 in a loaded or firing position, a rod engagement and release device and a security lock mechanism is provided as shown in FIGS. 5 and 6 and also in upper portions of FIGS. 4 and 7.

The rod engagement and release device comprises longitudinally mounted firing bar 17 extending through an opening 56 in an upper shell and having firing button 2 secured to firing bar 17 externally of the shell. Intermediate camming element 11 and lower firing catch 28 are mounted to engage lower part of cross bar 10 when cross bar 10 is in an upper spring-loaded position. To temporarily hold firing catch 28 engaged with cross bar 10, a camming surface is provided on camming bar 15, which is mounted to the back inner wall of shell 40 of mechanical device 1 to engage camming element 11 on firing bar 17, to provide sufficient frictional resistance between camming bar 15 and camming element 11 to hold cannula 22 and upper camming element 11 in the loaded or firing condition.

Mechanical firing device 1 preferably is provided with a securing device to prevent unexpected firing of biopsy device 50. Securing device features security locking bar 3 having cut-out 13 therein, of a width equal to the width of firing bar 17 and mounted within opposed openings in sides of shell 40 of firing device 1. This permits lateral movement of security locking bar 3 from a position engaging notch 12 in firing bar 17 to a position wherein cut-out 13 in the security locking bar is aligned with and permits movement of firing bar 17 through cut-out 13 of security locking bar 3. Button 2 may then be pushed to slide camming element 11 along camming bar 15, which in turn will release catch 28 from engagement with cross bar 10 and permit release of spring device 8 and movement of chamber 21 and cannula 22.

As spring device 8 is activated to move cannula 22 into the tissue, upper chamber 21 moves alongside of plug 23 in a manner to expand enlarged chamber 37 beneath plug 23 to produce a reduced or negative pressure within said chamber 37. Since enlarged chamber 37 is connected to annular passageway between stylet 18 and cannula 22, negative pressure of said enlarged chamber 37 will draw residual air in said annular passageway to likewise produce a negative pressure within cannula 22 about the tissue biopsy in the lumen 26. Thus the reduced or negative pressure in cannula 22 will function to hold the biopsy tissue sample within cannula 22 while cannula 22 is removed from the tissue being sampled.

An adjustable stopping arrangement is provided by lower stopping plate 7 to control depth of penetration of cannula 22. As previously mentioned the preferred depth of penetration is usually up to 22 cm. As shown in FIG. 4, lower stopping plate 7 is adjustable to a variety of positions. To control the position of stopping plate 7, a screw with tightening knob 4 is movable in channel 29 cut through a side wall of shell 40 and into threaded opening in the side of stopping plate 7, and a stud projecting from the other side of stopping plate 7 rides in slot 30 cut within the other side of the shell. Calibrations may be provided on one of the side walls of the mechanical device to assist in positioning of stopping plate 7. By securing lower stopping plate 7 in various positions, movement of cannula 22 and the upper chamber may be controlled to pre-selected positions in relation to said stylet contained within. This allows a very precise yet variable control of the depth of penetration of biopsy device 50.

As previously recited, in order to provide positive control of time of actuation of negative pressure biopsy needle, the biopsy needle of FIGS. 2 and 3 is positioned within slots in mechanical device 1, such that mechanical device 1 fixedly supports enlarged stylet head 20 while the cannula 22 and enlarged chamber 21 are mounted to a firing plate 5 for outward movement relative to stylet 18 and plug 23. When firing plate 5 is fired by movement of spring device 8, cannula 22 moves outwardly from point 25 of stylet 18, and zone 37 between plug 23 and intermediate annular section expands to produce a reduced or negative pressure in zone 37 and inside of cannula 22 as cannula 22 cores a biopsy. The control of extent of downward movement of enlarged chamber 21 and attached cannula 22 into the body is accomplished through vertical adjustment of lower stopping plate 7. The invention contemplates a fast release system of spring device 8, for accurate control of time of firing of cannula 22, and with a safety locking system to secure said firing system against premature release. This amount of negative vacuum pressure created within cannula 22 and enlarged chamber 37 is directly related to how fast device 50 is moved during firing. Internal vacuum pressure in device 50 is also related to diameter and length of cannula 22 and chamber 37.

With the present construction of negative pressure biopsy needle, the following preferred procedure to core and remove a biopsy specimen is contemplated. Pull ring 27 attached to firing plate 5 is manually moved outwardly relative to mounting device 1, thus compressing spring means 8 until cross bar 10 is moved up past the camming surface on firing catch 28, whereat firing catch 28 moves beneath cross bar 10 to latch firing plate 5 in a loaded position. To safeguard against accidental triggering, security locking bar 3 is slid laterally in slot 12 in firing bar 17 to a position where slot 13 is out of alignment with firing bar 17, thus preventing movement of firing bar 17. With stylet 18 mounted with point 25 slightly protruding from cannula 22 and plug 23 on stylet 18 within chamber 21, the cannula and stylet assembly is placed through door 1a into the slots in firing device 1. With mounting head 19 of chamber 21 engaged in semi-annular slot 26 in firing plate 5, and stylet plunger 20 held above slot 34 in fixed base plate 9, door 1a is closed to secure biopsy needle within the several slots. The biopsy needle is now loaded in firing device 1 for firing into a tissue to be sampled.

The sharpened end of cannula 22, with stylet 18 therein, is inserted into tissue to the depth at which it is desired to begin coring a biopsy. Thereafter, locking bar 3 is moved laterally to align slot 13 with firing bar 17 and firing button 2 is pressed to release spring means 8 which drives cannula 22 and jagged cutting edge 35 thereof out beyond point 25 of stylet 18 to core and contain a biopsy specimen within lumen of cannula 22, while, simultaneously, enlarged chamber 21 is driven along plug 23 to expand said enlarged chamber 37 below plug 23 to produce a negative pressure which will also draw air out of cannula 22 from around a cored biopsy to sever and hold the biopsy. To insure that the cored sample is completely severed, it is preferred to move device slightly to allow jagged cutting edge 35 to sever any portion of the sample that may remain connected. Mechanical device 1 with cannula 22 is then withdrawn, while the negative pressure continues to draw in and hold the biopsy sample within channel 36 of cannula 22.

The cover means 1a is then opened and cannula 22, enlarged chamber 21, and stylet 18 assembly is removed from the slots in mechanical device 1. Plunger 20 of stylet 18 is then moved toward cutting edge 35 of cannula 22, against the inner end of the biopsy, to force the biopsy out of cannula 22.

Alternately the biopsy may be removed from cannula 22 without removing cannula 22 or stylet assembly from the mechanical device, since an upward or loading movement of plunger 20 will also retract cannula 22 relative to the inner stylet, whereby the biopsy will no longer be within cannula 22.

The specific construction of a negative pressure biopsy needle shown in the drawings and in the above description is for exemplary purposes only. Various modifications in construction of biopsy needle, reduced pressure producing means, firing system, triggering devices and movement limiting elements may be made without departing from the scope and spirit of the invention.

I claim:

1. A device for obtaining a biopsy sample consisting essentially of:

a stationary stylet having proximal and distal ends and an intermediate area between said proximal and distal ends;

plug means having an aperture therethrough, first and second sides and inner and outer surfaces, said stylet extending through said aperture of said plug means, and said inner surface of said plug means being rigidly attached to said intermediate area of said stylet;

a hollow cannula having proximal and distal ends, a first chamber having an inner surface with a smaller diameter than said plug means, and a second chamber having an inner surface integral with and larger in diameter than said first chamber, said first and second chambers partially enclosing said stylet, said outer surface of said plug means being in sealed relation with said inner surface of said second chamber and being slidable relative thereto, said plug means defining an adjustable volume vacuum region between said plug means and said first chamber and a non-vacuum region within said second chamber, said first chamber being in fluid communication with said vacuum region of said second chamber and the diameters of each said chambers being substantially constant along their entire lengths;

means for coring a sample at said distal end of said cannula;

said cannula being movable from a first position where the distal end thereof is spaced from the distal end of said stylet and where the distal end of said stylet protrudes beyond the distal end of said cannula to a second position where the distal end there is extended in a direction away from said plug means and the distal end of said stylet is contained within said cannula, said stylet being substantially stationary during the movement of said cannula from said first to said second position such that the biopsy sample is cored by said coring means and simultaneously urged into and contained within said first chamber and a partial vacuum is created in said first chamber and said vacuum region of said second chamber due to the movement of said cannula from said first to said second position.

2. A biopsy device as in claim 1, wherein:

said distal end of said stylet and said distal end of said cannula each have sharpened cutting surfaces.

3. A biopsy device as in claim 2, wherein:

said cutting surface of said stylet has a conical shape, said cutting surface of said cannula is at an angle relative to a longitudinal axis of the device.

4. A biopsy device as in claim 1, further comprising:

an annular integral connection section between said first and second chambers of said cannula, a portion of said connecting section having a diameter smaller than that of said plug means, such that it limits axial movement of said plug means in the direction toward said first chamber.

5. The biopsy device as in claim 1, further comprising:

an annular flange formed on said cannula; and a plunger on said proximal end of said stylet.

6. A biopsy deice as in claim 1, further comprising:

means for moving said cannula from said first position to said second position.

7. A biopsy device as in claim 6, further comprising:

means for supporting and guiding said stylet and cannula.

8. A method of securing a biopsy sample from animal tissue, consisting essentially of the steps of:

providing a device having a first cutting means and a second cutting means, said first cutting means being partially contained within the second cutting means, said second cutting means being advanceable, said first cutting means having first and second chambers each having a substantially constant but different diameter, and a plug means in sealed relation within the second chamber and slidably mounted therein, said plug means dividing said second chamber into an adjustable volume vacuum region located between said first chamber and said plug means that is in fluid communication with said first chamber and a non-vacuum region that is not in fluid communication with said first chamber;

extending the first cutting means outwardly beyond the first cutting means;

inserting the device into the tissue to be sampled;

holding the first cutting means stationary and advancing the second cutting means further into the tissue so that a distal end of the first cutting means is spaced from the distal end of the second cutting means and contained within the second cutting means and such that said distal end of said second cutting means is spaced further away from said plug means that it was in said inserting step;

creating a partial vacuum within only the first chamber and said vacuum region of the second chamber during said holding and advancing step thereby simultaneously coring the biopsy sample and retaining the sample within the first cutting means; and removing the device from the tissue with the biopsy sample within the second cutting means.

9. The method of claim 8, wherein:

said step of advancing said second cutting means is carried out by a spring device.

10. The method of claim 9, wherein:

said spring device is actuated by a triggering means.

11. The method of claim 10, further comprising:

the step of providing an adjustable means for limiting the advancement of said cannula relative to said stylet in said holding and advancing step.

12. A device for obtaining a biopsy sample consisting essentially of:

a stylet having proximal and distal ends and an intermediate area between said proximal and distal ends;

plug means having an aperture therethrough, first and second sides and inner and outer surfaces, said stylet extending through said aperture of said plug means, and said inner surface of said plug means being rigidly attached to said intermediate area of said stylet;

a hollow cannula having proximal and distal ends, a first chamber having an inner surface with a smaller diameter than said plug means, and a second chamber having an inner surface integral with and larger in diameter than said first chamber, said first and second chambers partially enclosing said stylet, said outer surface of said plug means being in sealed relation with said inner surface of said second chamber and being slidable relative thereto, said first chamber being in fluid communication with a portion of said second chamber and the diameters of each said chambers being substantially constant along their entire lengths;

means for coring a sample at said distal end of said cannula;

said cannula being movable from a first position where the distal end thereof is spaced from the distal end of said stylet and where the distal end of said stylet protrudes beyond the distal end of said cannula to a second position where the distal end thereof is extended in a direction away from said plug means and the distal end of said stylet is contained within said cannula, said stylet being substantially stationary during the movement of said cannula from said first to said second position such that the biopsy sample is cored by said coring means and simultaneously urged into and contained within said first chamber and a partial vacuum is created in said first chamber and a portion of said second chamber due to the movement of said cannula from said first to said second position;

means for moving said cannula from said first position to said second position;

said moving means including means for supporting and holding said stylet in a fixed position; and means for supporting and guiding said stylet and cannula.

13. The biopsy device as in claim 12, wherein:

said moving means includes triggering means for selectively actuating said moving means.

14. a locking means to secure said triggering mans against accidental release.

15. The biopsy device of claim 12, further comprising means for reloading said moving means after it has been actuated.

16. The biopsy device of claim 12, wherein:

said moving means includes adjustable means for precisely limiting the movement of said cannula relative to said stylet.

17. The biopsy device of claim 12, wherein:

said moving means has an outer surface and an access opening formed therein to allow said stylet and said cannula to be selectively inserted and removed from said moving means.

18. The biopsy device of claim 12, further comprising:

cover means mounted over said access opening for covering said access opening.

* * * * *